(12) United States Patent
Penn et al.

(10) Patent No.: US 8,075,609 B2
(45) Date of Patent: Dec. 13, 2011

(54) EXPANDABLE STENT

(75) Inventors: Ian M. Penn, Vancouver (CA); Donald R. Ricci, Vancouver (CA); George A. Shukov, Lost Altos, CA (US)

(73) Assignee: evYsio Medical Devices ULC (CA)

( * ) Notice: Subject to any disclaimer, the term of this patent is extended or adjusted under 35 U.S.C. 154(b) by 1275 days.

(21) Appl. No.: 10/850,397

(22) Filed: May 21, 2004

(65) Prior Publication Data

US 2004/0215325 A1 Oct. 28, 2004

Related U.S. Application Data

(63) Continuation of application No. 09/462,461, filed as application No. PCT/CA98/00646 on Jul. 8, 1998, now Pat. No. 6,796,997, application No. 10/850,397, which is a continuation-in-part of application No. 09/142,508, filed as application No. PCT/CA97/00151 on Mar. 5, 1997, now Pat. No. 6,217,608.

(60) Provisional application No. 60/051,953, filed on Jul. 8, 1997.

(30) Foreign Application Priority Data

| Mar. 5, 1996 | (CA) | 2171047 |
| May 3, 1996 | (CA) | 2175722 |
| Sep. 17, 1996 | (CA) | 2185740 |
| Dec. 10, 1996 | (CA) | 2192520 |

(51) Int. Cl.
*A61F 2/06* (2006.01)
(52) U.S. Cl. .................................................. 623/1.15
(58) Field of Classification Search .................. 623/1.15, 623/1.17, 1.2, 1.22, 1.3; 606/108
See application file for complete search history.

(56) References Cited

U.S. PATENT DOCUMENTS

| 3,657,774 A | 4/1972 | Reynolds ..................... 24/73 CF |
| 3,993,078 A | 11/1976 | Bergentz et al. .......... 128/334 R |
| 4,503,569 A | 3/1985 | Dotter ................................. 3/1.4 |
| 4,553,545 A | 11/1985 | Maass et al. .................. 128/341 |

(Continued)

FOREIGN PATENT DOCUMENTS

CA 1239755 8/1988

(Continued)

OTHER PUBLICATIONS

EPO decision revoking European Patent No. EP-B-0888093, Dec. 17, 2003.

(Continued)

*Primary Examiner* — Corrine M McDermott
*Assistant Examiner* — Gregory Anderson
(74) *Attorney, Agent, or Firm* — Katten Muchin Rosenman LLP

(57) ABSTRACT

An expandable stent comprising a proximal end and a distal end in communication with one another, a tubular wall disposed between the proximal end and the distal end, the tubular wall having a longitudinal axis and a porous surface defined by a plurality of interconnected struts, the interconnected struts comprising a gradient of strut thickness from a first end to a second end of the tubular wall, the stent being expandable from a first, contracted position to a second, expanded position upon the application of a radially outward force on the stent. The stent is ideally suited for applications in which a tortuous pathway must be followed to the stenosis or blockage and in which high radial rigidity of the expanded stent is required e.g., the treatment of ostial stenosis.

28 Claims, 1 Drawing Sheet

U.S. PATENT DOCUMENTS

| | | | | |
|---|---|---|---|---|
| 4,580,568 A | 4/1986 | Gianturco | | 128/345 |
| 4,655,771 A | 4/1987 | Wallsten | | 623/1 |
| 4,681,110 A | 7/1987 | Wiktor | | 128/343 |
| 4,733,665 A | 3/1988 | Palmaz | | 128/343 |
| 4,739,762 A | 4/1988 | Palmaz | | 128/343 |
| 4,762,128 A | 8/1988 | Rosenbluth | | 128/343 |
| 4,768,507 A | 9/1988 | Fischell et al. | | 128/303 R |
| 4,795,458 A | 1/1989 | Regan | | 623/1 |
| 4,800,882 A | 1/1989 | Gianturco | | 128/343 |
| 4,830,003 A | 5/1989 | Wolff et al. | | 128/343 |
| 4,856,516 A | 8/1989 | Hillstead | | 128/343 |
| 4,878,906 A | 11/1989 | Lindemann et al. | | 623/1 |
| 4,886,062 A | 12/1989 | Wiktor | | 128/343 |
| 4,907,336 A | 3/1990 | Gianturco | | 29/515 |
| 4,954,126 A | 9/1990 | Wallstén | | 600/36 |
| 4,969,458 A | 11/1990 | Wiktor | | 606/194 |
| 4,994,071 A | 2/1991 | MacGregor | | 606/194 |
| 5,019,085 A | 5/1991 | Hillstead | | 606/108 |
| 5,019,090 A | 5/1991 | Pinchuk | | |
| 5,035,706 A | 7/1991 | Giantureo et al. | | 606/198 |
| 5,037,392 A | 8/1991 | Hillstead | | 604/96 |
| 5,041,126 A | 8/1991 | Gianturco | | 606/195 |
| 5,061,275 A | 10/1991 | Wallstén et al. | | 623/1 |
| 5,073,694 A | 12/1991 | Tessier et al. | | |
| 5,102,417 A | 4/1992 | Palmaz | | 606/195 |
| 5,104,404 A | 4/1992 | Wolff | | 623/1 |
| 5,108,417 A | 4/1992 | Sawyer | | 606/198 |
| 5,116,365 A | 5/1992 | Hillstead | | 623/1 |
| 5,133,732 A | 7/1992 | Wiktor | | 606/195 |
| 5,135,536 A | 8/1992 | Hillstead | | 606/195 |
| 5,139,480 A | 8/1992 | Hickle et al. | | 604/8 |
| 5,147,385 A | 9/1992 | Beck et al. | | 623/1 |
| 5,161,547 A | 11/1992 | Tower | | 128/898 |
| 5,192,307 A | 3/1993 | Wall | | 623/1 |
| 5,195,984 A | 3/1993 | Schatz | | 606/195 |
| 5,197,987 A | 3/1993 | Koch et al. | | 623/20 |
| 5,201,901 A | 4/1993 | Harada et al. | | 606/198 |
| 5,266,073 A | 11/1993 | Wall | | 623/1 |
| 5,269,802 A | 12/1993 | Garber | | 606/191 |
| 5,282,823 A | 2/1994 | Schwartz et al. | | 606/198 |
| 5,282,824 A | 2/1994 | Gianturco | | 606/198 |
| 5,290,305 A | 3/1994 | Inoue | | 606/191 |
| 5,292,331 A | 3/1994 | Boneau | | 606/198 |
| 5,314,472 A | 5/1994 | Fontaine | | 623/12 |
| 5,316,023 A | 5/1994 | Palmaz et al. | | 128/898 |
| 5,342,387 A | 8/1994 | Summers | | 606/198 |
| 5,345,057 A | 9/1994 | Muller | | |
| 5,383,892 A | 1/1995 | Cardon et al. | | 606/198 |
| 5,395,390 A | 3/1995 | Simon et al. | | 606/198 |
| 5,397,355 A | 3/1995 | Marin et al. | | |
| 5,405,377 A | 4/1995 | Cragg | | 623/1 |
| 5,421,955 A | 6/1995 | Lau et al. | | 216/48 |
| 5,443,498 A | 8/1995 | Fontaine | | 623/1 |
| 5,443,500 A | 8/1995 | Sigwart | | 623/1 |
| 5,449,373 A | 9/1995 | Pinchasik et al. | | 606/198 |
| 5,458,615 A | 10/1995 | Klemm et al. | | 606/198 |
| 5,496,365 A | 3/1996 | Sgro | | 623/1 |
| 5,507,767 A | 4/1996 | Maeda et al. | | 606/198 |
| 5,507,771 A | 4/1996 | Gianturco | | 606/198 |
| 5,514,154 A | 5/1996 | Lau et al. | | 606/195 |
| 5,522,880 A | 6/1996 | Barone et al. | | 623/1 |
| 5,527,354 A | 6/1996 | Fontaine et al. | | 623/1 |
| 5,540,712 A | 7/1996 | Kleshinski et al. | | 606/198 |
| 5,569,295 A | 10/1996 | Lam | | 606/198 |
| 5,575,771 A | 11/1996 | Walinsky | | 604/96 |
| 5,575,817 A | 11/1996 | Martin | | 623/1 |
| 5,591,197 A | 1/1997 | Orth et al. | | 606/198 |
| 5,603,721 A | 2/1997 | Lau et al. | | 606/195 |
| 5,607,442 A | 3/1997 | Fischell et al. | | 606/191 |
| 5,623,771 A | 4/1997 | Winheim | | 34/585 |
| 5,628,787 A | 5/1997 | Mayer | | 623/1 |
| 5,634,941 A | 6/1997 | Winston et al. | | 623/1 |
| 5,639,278 A | 6/1997 | Dereume et al. | | 623/1 |
| 5,643,312 A | 7/1997 | Fischell et al. | | 606/198 |
| 5,643,340 A | 7/1997 | Nunokawa | | 623/1 |
| 5,653,743 A | 8/1997 | Martin | | 623/1 |
| 5,674,278 A | 10/1997 | Boneau | | 623/1 |
| 5,676,696 A | 10/1997 | Marcade | | 623/1 |
| 5,676,697 A | 10/1997 | McDonald | | 623/1 |
| 5,693,086 A | 12/1997 | Goicoechea et al. | | 623/1 |
| 5,697,971 A | 12/1997 | Fischell et al. | | 623/1 |
| 5,709,712 A | 1/1998 | Paul et al. | | 607/27 |
| 5,733,303 A | 3/1998 | Israel et al. | | 606/198 |
| 5,755,734 A | 5/1998 | Richter et al. | | 606/194 |
| 5,755,735 A | 5/1998 | Richter et al. | | 606/194 |
| 5,755,771 A | 5/1998 | Penn et al. | | 623/1 |
| 5,776,161 A | 7/1998 | Globerman | | 606/194 |
| 5,807,404 A | 9/1998 | Richter | | 623/1 |
| 5,824,040 A | 10/1998 | Cox et al. | | 623/1 |
| 5,827,320 A | 10/1998 | Richter et al. | | 606/194 |
| 5,827,321 A | 10/1998 | Roubin | | 606/195 |
| 5,836,964 A | 11/1998 | Richter et al. | | 606/194 |
| 5,836,966 A | 11/1998 | St. Germain | | 606/198 |
| 5,843,117 A | 12/1998 | Alt et al. | | |
| 5,843,120 A | 12/1998 | Israel et al. | | 606/198 |
| 5,868,783 A | 2/1999 | Tower | | 606/198 |
| 5,879,370 A | 3/1999 | Fischell et al. | | 606/198 |
| 5,902,332 A | 5/1999 | Schatz | | 623/1 |
| 5,906,640 A | 5/1999 | Penn et al. | | 623/1 |
| 5,906,759 A | 5/1999 | Richter | | 219/121.63 |
| 5,911,754 A | 6/1999 | Kanesaka et al. | | 623/1 |
| 5,913,895 A | 6/1999 | Burpee et al. | | 623/1 |
| 5,922,005 A | 7/1999 | Richter et al. | | 606/192 |
| 5,922,020 A | 7/1999 | Klein et al. | | 623/1 |
| 5,922,021 A * | 7/1999 | Jang | | 623/1.15 |
| 5,925,061 A | 7/1999 | Ogi et al. | | |
| 5,931,866 A | 8/1999 | Frantzen | | 623/1 |
| 5,964,770 A | 10/1999 | Flomenblit et al. | | 606/78 |
| 5,964,798 A | 10/1999 | Imran | | 623/1 |
| 5,980,552 A | 11/1999 | Pinchasik et al. | | 606/198 |
| 5,997,703 A | 12/1999 | Richter | | 204/297 |
| 6,017,362 A | 1/2000 | Lau | | 623/1 |
| 6,017,365 A | 1/2000 | Von Oepen | | 623/1 |
| 6,027,526 A * | 2/2000 | Limon et al. | | 623/1.15 |
| 6,033,433 A | 3/2000 | Ehr et al. | | 623/1 |
| 6,042,597 A | 3/2000 | Kveen et al. | | 606/198 |
| 6,053,940 A | 4/2000 | Wijay | | 623/1 |
| 6,059,811 A | 5/2000 | Pinchasik et al. | | 606/198 |
| 6,066,169 A | 5/2000 | McGuinness | | 623/1.16 |
| 6,068,656 A | 5/2000 | Von Oepen | | 623/1.17 |
| 6,083,259 A | 7/2000 | Frantzen | | 623/1.15 |
| 6,086,604 A | 7/2000 | Fischell et al. | | 606/198 |
| 6,090,127 A | 7/2000 | Globerman | | 606/194 |
| 6,090,133 A | 7/2000 | Richter et al. | | 623/1 |
| 6,099,455 A | 8/2000 | Columbo et al. | | 600/3 |
| 6,106,548 A | 8/2000 | Roubin et al. | | 623/1.15 |
| 6,114,049 A | 9/2000 | Richter | | 428/571 |
| 6,117,156 A | 9/2000 | Richter et al. | | 606/194 |
| 6,117,165 A | 9/2000 | Becker | | 623/1 |
| 6,123,721 A | 9/2000 | Jang | | 623/1 |
| 6,129,754 A | 10/2000 | Kanesaka et al. | | 623/1 |
| 6,156,052 A | 12/2000 | Richter et al. | | 606/191 |
| 6,159,237 A | 12/2000 | Alt et al. | | 623/1.11 |
| 6,171,334 B1 | 1/2001 | Cox | | 623/1.15 |
| 6,179,867 B1 | 1/2001 | Cox | | 623/1.15 |
| 6,179,868 B1 | 1/2001 | Burpee et al. | | 623/1.17 |
| 6,183,507 B1 | 2/2001 | Lashinski et al. | | 623/1.15 |
| 6,190,403 B1 | 2/2001 | Fischell et al. | | 623/1 |
| 6,190,405 B1 | 2/2001 | Culombo et al. | | 623/1.15 |
| 6,190,406 B1 | 2/2001 | Duerig et al. | | 623/1.23 |
| 6,193,744 B1 | 2/2001 | Ehr et al. | | 623/1 |
| 6,193,747 B1 | 2/2001 | von Oepen | | 623/1.15 |
| 6,197,048 B1 | 3/2001 | Richter | | 623/1.15 |
| 6,200,334 B1 | 3/2001 | Jang | | 623/1.1 |
| 6,203,569 B1 | 3/2001 | Wijay | | 623/1.15 |
| 6,231,598 B1 | 5/2001 | Berry et al. | | 623/1.15 |
| 6,238,401 B1 | 5/2001 | Richter | | 606/108 |
| 6,251,133 B1 | 6/2001 | Richter et al. | | 623/1.16 |
| 6,273,911 B1 | 8/2001 | Cox et al. | | 623/1.15 |
| 6,287,336 B1 | 9/2001 | Globerman et al. | | 623/1.3 |
| 6,299,755 B1 | 10/2001 | Richter | | 205/651 |
| 6,315,794 B1 | 11/2001 | Richter | | 623/1.34 |
| 6,355,059 B1 | 3/2002 | Richter et al. | | 623/1.17 |
| 6,375,677 B1 | 4/2002 | Penn et al. | | 623/1.16 |
| 6,547,817 B1 | 4/2003 | Fischell et al. | | 623/1.16 |
| 2001/0000043 A1 | 3/2001 | Israel et al. | | 606/198 |

| | | | |
|---|---|---|---|
| 2001/0001317 | A1 | 5/2001 | Duerig et al. ............... 623/1.15 |
| 2002/0052646 | A1 | 5/2002 | Fischell et al. ............... 623/1.15 |
| 2003/0114868 | A1 | 6/2003 | Fischell et al. ............... 606/159 |

FOREIGN PATENT DOCUMENTS

| | | |
|---|---|---|
| CA | 1245527 | 11/1988 |
| CA | 2134997 | 5/1996 |
| CA | 2171047 | 9/1997 |
| CA | 2200118 A1 | 9/1997 |
| CA | 2188233 A1 | 10/1997 |
| CA | 2175722 | 11/1997 |
| CA | 2185740 | 3/1998 |
| CA | 2288044 A1 | 11/1998 |
| DE | 295 16712 U1 | 8/1996 |
| EP | 0 045 627 | 10/1982 |
| EP | 0 364 787 A1 | 4/1990 |
| EP | 0 505 686 A1 | 9/1992 |
| EP | 0 566 807 A1 | 10/1993 |
| EP | 0 709 067 A2 | 5/1995 |
| EP | 0 669 114 A1 | 8/1995 |
| EP | 0 679 372 A2 | 11/1995 |
| EP | 0 714 641 A2 | 6/1996 |
| EP | 0 732 088 A2 | 9/1996 |
| FR | 2678508 | 1/1993 |
| JP | 06-181993 A | 5/1994 |
| JP | 6-41745 | 6/1994 |
| JP | 08-196642 A | 6/1996 |
| JP | 09-285548 A | 11/1997 |
| JP | 10-52503 A | 2/1998 |
| WO | WO 94/12136 | 6/1994 |
| WO | WO 95/09584 | 4/1995 |
| WO | 95/26695 A2 | 10/1995 |
| WO | 95/31945 A1 | 11/1995 |
| WO | WO 95/31945 A1 | 11/1995 |
| WO | WO 96/02295 A1 | 2/1996 |
| WO | WO 96/03092 A1 | 2/1996 |
| WO | WO 96/14028 | 5/1996 |
| WO | 96/33757 A1 | 10/1996 |
| WO | WO 97/04721 | 2/1997 |
| WO | 97/26840 A1 | 7/1997 |
| WO | WO 97/32543 | 9/1997 |
| WO | WO 97/32544 | 9/1997 |
| WO | WO 97/33532 | 9/1997 |
| WO | WO 98/22159 A3 | 5/1998 |
| WO | WO 98/30173 | 7/1998 |
| WO | WO 98/33546 | 8/1998 |
| WO | 99/02105 A1 | 1/1999 |
| WO | WO 00/28922 | 5/2000 |
| WO | WO 00/49971 | 8/2000 |
| WO | WO 00/53112 | 9/2000 |
| WO | WO 01/00112 A1 | 1/2001 |
| WO | WO 01/15632 A1 | 3/2001 |

OTHER PUBLICATIONS

Lawrence et al., "Percutaneous Endovascular Graft: Experimental Evaluation," 1987 RSNA Annual Meeting, Radiology, vol. 163, pp. 357-360 (May 1987).

Mirich et al., "Percutaneously Placed Endovascular Grafts for Aortic Aneurysms: Feasibility Study," Radiology, vol. 170, pp. 1033-1037 (1989).

Fallone et al., "Elastic Characteristics of the Self-Expanding Metallic Stents," Investigative Radiology, vol. 23, pp. 370-376 (May 1988).

Charnsangavej et al., "Stenosis of the Vena Cava: Preliminary Assessment of Treatment with Expandable Metallic Stents," Radiology, 1986 161:295-98.

Rösch et al., "Gianturco Expandable Stents in Experimental and Clinical Use," Mar. 24, 1987, pp. 121-124.

Wallace, et al., "Tracheobronchial Tree: Expandable Metallic Stents Used in Experimental and Clinical Applications—Work in Progress," Radiology, 158:309-12 (1986).

Rösch et al., "Experimental Intrahepatic Protacaval Anastomosis: Use of Expandable Gianturco Stents," Radiology, 162:481-85 (1987).

Rösch et al., "Modified Gianturco Expandable Wire Stents in Experimental and Clinical Use," Ann Radiol., 31:100-03 (1988).

Charnsangavej et al., "A New Expandable Metallic Stent for Dilatation of Stenotic Tubular Structures: Experimental and Clinical Evaluation," Houston Medical Journal, vol. 3, Jun. 1987, pp. 41-51.

Rösch et al., "Gianturco Expandable Wire Stents in the Treatment of Superior Vena Cava Syndrome Recurring After Maximum-Tolerance Radiation," Cancer, 60:1243-46 (1987).

Yoshioka et al., "Self-Expanding Endovascular Graft: An Experimental Study in Dogs," AJR, 151:673-76 (1988).

Simonds et al., "Use of Expandable Metal Stents in the Treatment of Bronchial Obstruction," Thorax, 44:680-81 (1989).

Duprat et al., "Flexible Balloon-Expanded Stent for Small Vessels—Work in Progress," Radiology, 162:276-78 (1987).

Second Thoraxcenter Course on Coronary Stenting, Rotterdam, the Netherlands, Dec. 13-16, 1995 .

John H.K. Vogel, M.D. and Spencer B. King III, M.D. (Editors), The Practice of Interventional Cardiology, Second Edition, chapter 29—Stents for Bailout and Restenosis, pp. 301-306, 1993.

Declaration of Jerome Segal, M.D., Feb. 2, 2006.

LPL Systems Inc. System 2000 Stent Cutter from the LPL Systems, Inc web page at <http://www.lplsystems.com/stent_cutter.html> retrieved on Nov. 8, 2004.

LPL Systems, Inc. Invoice, Quote No. 11295, Date Nov. 29, 1995.

Declaration of Charles A. Taylor, Nov. 9, 2004.

Declaration of Richard J. Saunders Regarding European Patent EP 1 066 804, Jan. 28, 2006.

Oct. 31, 2003 Office Action from the Australian Patent Office for Australian Patent Application No. 3307/02.

Oct. 31, 2003 Office Action from the Australian Patent Office for Australian Patent Application No. 34317/02.

Jun. 27, 2008 Office Action from the Canadian Patent Office for Canadian Patent Application No. 2,295,682.

Sep. 29, 2006 Office Action from the Canadian Patent Office for Canadian Patent Application No. 2,295,682.

Jan. 3, 2006 Office Action from the Canadian Patent Office for Canadian Patent Application No. 2,295,682.

Aug. 23, 2001 Office Action from the European Patent Office for European Patent Application No. 98 931 852.2.

Jul. 3, 2007 Office Action from the Japanese Patent Office for Japanese Patent Application No. 2000-501709.

Jul. Mar. 25, 2008 Office Action from the Japanese Patent Office for Japanese Patent Application No. 2000-501709.

Jul. 20, 2010 Office Action from the Japanese Patent Office for Japanese Patent Application No. 2000-501709.

Apr. 3, 2002 Office Action from the New Zealand Patent Office for New Zealand Patent Application No. 517969.

Sep. 26, 2000 Office Action from the New Zealand Patent Office for New Zealand Patent Application No. 502727.

Apr. 3, 2002 Office Action from the New Zealand Patent Office for New Zealand Patent Application No. 502727.

* cited by examiner though these prior art stents have achieved a varying degree
EXPANDABLE STENT This is a continuation of application Ser. No. 09/462,461, now U.S. Pat. No. 6,796,997, filed Jun. 12, 2000, which is a 371 of PCT/CA98/00646 (designating the U.S.), filed Jul. 8, 1998, which claims benefit of U.S. Application No. 60/051,953, filed Jul. 8, 1997. This application is also a continuation-in-part of application Ser. No. 09/142,508, filed Feb. 16, 1999, now U.S. Pat. No. 6,217,608, issued Apr. 17, 2001, which is a 371 of PCT/CA97/00151, filed Mar. 5, 1997 (designating the U.S.; and which published in English in WO 97/32543 on Sep. 12, 1997), which claims benefit of (i) CA 2,171,047, filed Mar. 5, 1996, (ii) CA 2,175,722, filed May 3, 1996, (iii) CA 2,185,740, filed Sep. 17, 1996, and (iv) CA 2,192,520, filed Dec. 10, 1996. The contents of each of the above are incorporated herein by reference.

TECHNICAL FIELD

The present invention relates to an expandable stent.

BACKGROUND ART

Stents are generally known. Indeed, the term "stent" has been used interchangeably with terms such as "intraluminal vascular graft" and "expansible prosthesis". As used throughout this specification the term "stent" is intended to have a broad meaning and encompasses any expandable prosthetic device for implantation in a body passageway (e.g., a lumen or artery).

In the past eight to ten years, the use of stents has attracted an increasing amount of attention due to the potential of these devices to be used, in certain cases, as an alternative to surgery. Generally, a stent is used to obtain and maintain the patency of the body passageway while maintaining the integrity of the passageway. As used in this specification, the term "body passageway" is intended to have a broad meaning and encompasses any duct (e.g., natural or introgenic) within the human body and can include a member selected from the group comprising: blood vessels, respiratory ducts, gastrointestinal ducts and the like.

Initial stents were balloon deployable of self-expanding, spring-like devices which were inserted in the body passageway in a contracted state.

In the case of self-expanding, spring-like devices, when released, the stent would automatically expand and increase to a final diameter dependent on the size of the stent and the elasticity of the body passageway. An example of such a stent is known in the art as the Wallstent™.

The self-expanding stents were found by some investigators to be deficient since, when deployed, they could place undue, permanent stress on the walls of the body passageway. Further, upon expansion, the stent would shorten in length in an unpredictable fashion thereby reducing the reliability of the stent.

This led to the development of various stents which were controllably expandable at the target body passageway so that only sufficient force to maintain the patency of the body passageway was applied in expanding the stent. Generally, in the balloon-deployable systems, a stent, in association with a balloon, is delivered to the target area of the body passageway by a catheter system. Once the stent has been properly located (for example, for intravascular implantation the target area of the vessel can be filled with a contract medium to facilitate visualization during fluoroscopy), the balloon is expanded thereby expanding the stent by plastic deformation so that the latter is urged in place against the body passageway. As indicated above, the amount of force applied is at least that necessary to maintain the patency of the body passageway. At this point, the balloon is deflated and withdrawn within the catheter, and subsequently removed.

Ideally, the stent will remain in place and maintain the target area of the body passageway substantially free of blockage (or narrowing).

A stent which has gained some notoriety in the art is known as the Palmaz-SchatzT Balloon Expandable Stent (hereinafter referred to as "the Palmaz-Schatz stent"). This stent is discussed in a number of patents including U.S. Pat. Nos. 4,733,665, 4,739,762, 5,102,417 and 5,316,023, the contents of each of which are hereby incorporated by reference.

Another stent which has gained some notoriety in the art is known as the Gianturco-RoubinFlex-Stent™ (hereinafter referred to as "the Gianturco-Roubin stent"). This stent is discussed in a number of patents, including U.S. Pat. Nos. 4,800,882, 4,907,336 and 5,041,126, the contents of each of which are hereby incorporated by reference.

Other types of stents are disclosed in the following patents:
U.S. Pat. No. 5,035,706 (Gianturco et al.),
U.S. Pat. No. 5,037,392 (Hillstead),
U.S. Pat. No. 5,147,385 (Beck et al),
U.S. Pat. No. 5,282,824 (Gianturco),
Canadian Patent No. 1,239,755 (Wallsten), and
Canadian Patent No. 1,245,527 (Gianturco et al.) the contents of which are hereby incorporated by reference.

While these prior art stents have achieved a varying degree of success, the art is constantly in need of new stents having improved flexibility and stability while being able to be readily implanted with little or no trauma to the target lumen.

An improved expandable stent is described in the following copending patent applications:

Canadian Patent Application Number 2,134,997 (filed Nov. 3, 1994); Canadian Patent Application Number 2,171,047 (filed Mar. 5, 1996); Canadian Patent Application Number 2,175,722 (filed May 3, 1996); Canadian Patent Application Number 2,185,740 (filed Sep. 17, 1996); International Patent Application PCT/CA97/00151 (filed Mar. 5, 1997); and International Patent Application PCT/CA97/00152 (filed Mar. 5, 1997; the contents of each of which are hereby incorporated by reference (hereinafter collectively referred to as "the Divysio applications"). Generally, the stent illustrated in the Divysio applications comprises a tubular wall disposed between the proximal end and the distal end. The tubular wall has a longitudinal axis and a porous surface defined by a plurality intersecting members arranged to define a first repeating pattern. The first repeating pattern comprises a polygon having a pair of side walls substantially parallel to the longitudinal axis. A first concave shaped wall and a second convex-shaped wall connect the side walls. The stent is expandable from a first, contracted position to a second, expanded position upon the application of a radially outward force exerted on the stent.

While the stents disclosed in the Divysio applications represent an advance in the art, there is still room for improvement.

One specific area in which improvement is desirable is in the treatment of ostial stenosis (these typically occur in the coronary arteries, vein grafts and renal arteries). As is known in the art (and discussed in more detail with reference in FIG. 11 in International Patent Applications PCT/CA97/00151 and PCT/CA97/00152 referred to hereinabove), ostial stenosis occurs as a result of narrowing of the ostial segment of the right coronary artery. Ideally, a stent capable of implantation into such an ostial stenosis must be of sufficient rigidity after expansion to resist the elastic recoil of the ostial blockage. However, a stent of such sufficient rigidity will likely be deficient since it will either: (i) be retarded in its advance along the artery due to the sharp bend in the right coronary artery, or (ii) traverse the sharp bend in the right coronary artery but subsequently straighten the distal portion of the right coronary artery thereby increasing the likelihood of tearing the artery. Conversely, a stent of sufficient flexibility to traverse the sharp bend in the right coronary artery is susceptible to recoil in the ostial right coronary artery. Accordingly, to the knowledge of the inventors, there is no known effective manner by which a stent may be used to treat a conventional ostial stenosis.

Accordingly, it would be desirable to have an improved stent which overcomes these disadvantages. It would also be desirable if such stent was relatively easy to implant. It would be further desirable if such a stent were capable of being uniformly expanded at relatively low pressure while obviating or mitigating longitudinal shrinkage thereof. It would be further desirable if such a stent were not susceptible to asymmetric internal coverage of the body passageway, a problem associated with "coil"-type stents—see, for example, U.S. Pat. No. 5,282,824 (Gianturco). It would be further desirable if such a stent was not susceptible to movement along the longitudinal axis of the body passageway during or after implantation. It would be further desirable if such a stent was characterized by a desirable balance of lateral flexibility in the unexpanded state and radial rigidity in the expanded state.

SUMMARY OF THE INVENTION

It is an object of the present invention to provide a novel expandable stent which obviates or mitigates at least one of the above-mentioned disadvantages of the prior art.

Accordingly, in one of its aspects, the present invention provides an expandable stent comprising a proximal end and a distal end in communication with one another, a tubular wall disposed between the proximal end and the distal end, the tubular wall having a longitudinal axis and a porous surface defined by a plurality of interconnected struts, the interconnected struts comprising a gradient of strut thickness from a first end to a second end of the tubular wall, the stent being expandable from a first, contracted position to a second, expanded position upon the application of a radially outward force on the stent.

Thus, in this aspect of the present invention, also known as the "strut gradient embodiment", we have discovered that, by varying the thickness of the network of struts along the length of tubular wall of the stent, it is possible to produce a stent having progressively changing relative flexibility (referred to throughout this specification as the "progressi-flex" property of the present stent) along its length without the need to alter the specific design of the network of struts. The principal advantage of this progressi-flex property of the present stent may be conferred to many otherwise conventional stent designs while retaining unaffected the benefits accruing from the specific conventional stent design.

In another of its aspects, the present invention provides an expandable stent comprising a proximal end and a distal end in communication with one another, a tubular wall disposed between the proximal end and the distal end, the tubular wall having a longitudinal axis and a porous surface defined by a plurality of interconnected struts, the interconnected struts defining a plurality of interconnected circumferentially disposed rings of a first repeating pattern, the plurality of interconnected circumferentially disposed rings comprising a first repeating pattern amplitude gradient from a first end to a second end of the tubular wall, the stent being expandable from a first, contracted position to a second, expanded position upon the application of a radially outward force on the stent.

In this aspect of the invention, also known as the "amplitude gradient embodiment", it has been discovered that the progressi-flex property referred to above with referred to the strut thickness embodiment, may be conferred to a stent without the need to incorporate the gradient of strut thickness provided that the stent has a series of interconnected circumferentially disposed rings of a repeating pattern which have a repeating pattern amplitude gradient. The term "repeating pattern amplitude gradient", as used throughout this specification, is intended to mean a variance (i.e., an increase or decrease) in the amplitude of the repeating pattern in each circumferentially disposed ring in the network of interconnected struts making up the stent structure.

The present stent is ideally suited for applications in which a tortuous pathway must be followed to the stenosis or blockage and in which high radial rigidity of the expanded stent is required—e.g., the treatment of ostial stenosis.

BRIEF DESCRIPTION OF THE DRAWINGS

Embodiments of the present invention will be described with reference to the accompanying drawing, in which.

BEST MODE FOR CARRYING OUT THE INVENTION

Figure 1:
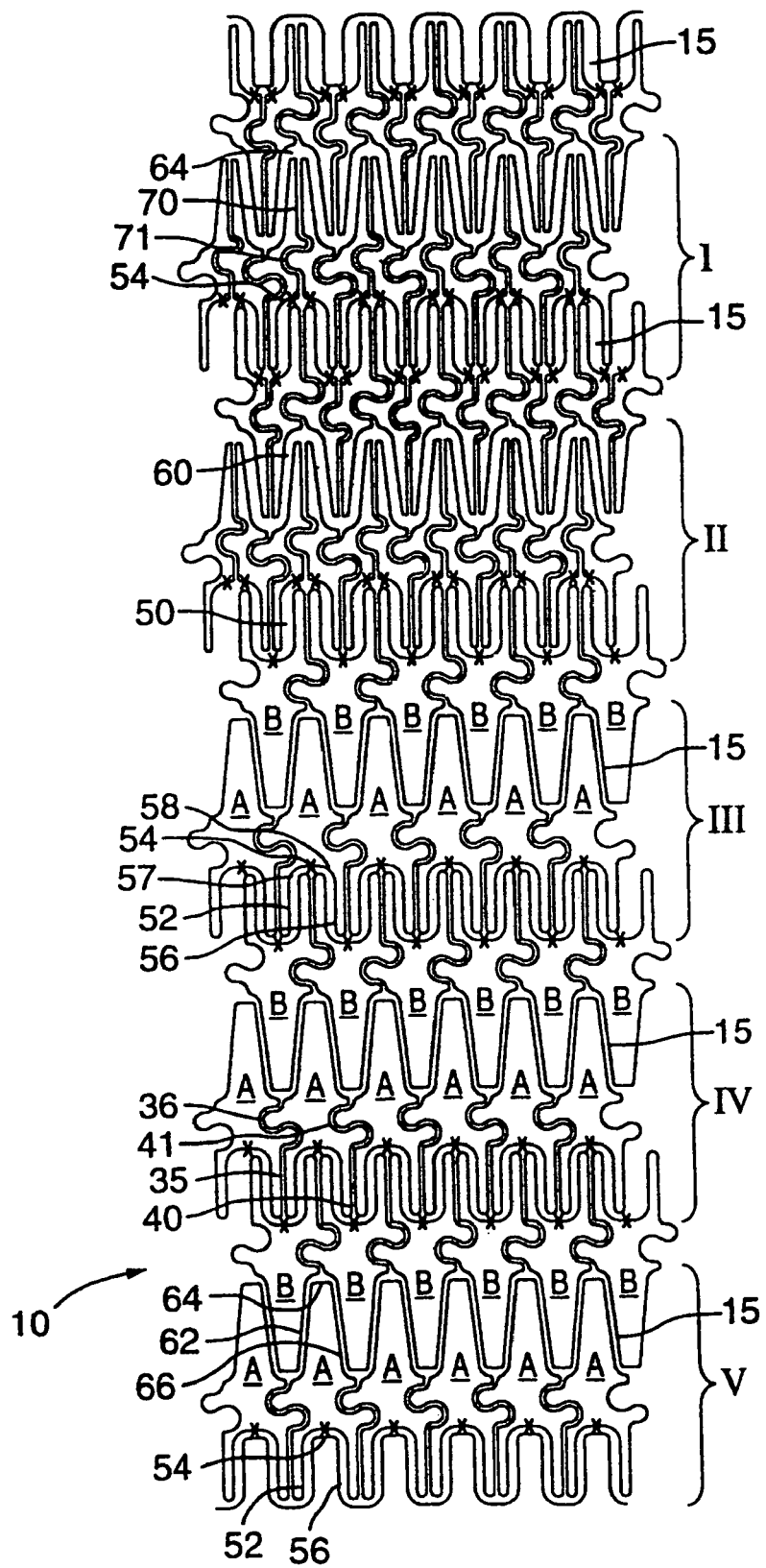
FIG. 1 illustrates a two dimensional representation of a preferred embodiment of a repeating pattern useful in the stent of the present invention.

Initially, the strut gradient embodiment will be discussed.

As used throughout this specification, the term "gradient of strut thickness" is intended to mean a variance in strut thickness (i.e., an increase or decrease) in the network of interconnected struts making up the stent structure.

Further, as used throughout this specification, the term "porosity" is intended to mean the polygonal openings defined by the network of interconnected struts comprised in the tubular wall of the stent.

Preferably the present stent comprises a plurality of circumferentially disposed rings of a repeating pattern of struts. In this embodiment, it is preferred that the gradient of strut thickness is manifested between adjacent circumferentially disposed rings of the repeating pattern of struts. In other words, it is preferred that, in a given circumferentially disposed ring of the repeating pattern, the struts are of a substantially uniform thickness and that the gradient of strut thickness (i.e., the increase or decrease of strut thickness) is manifested from ring to ring.

It has been found that a gradient of strut thickness (i.e., the increase or decrease of strut thickness), for example from ring to ring, in the range of from about 5% to about 50%, preferably from about 10% to about 40%, more preferably from about 15% to about 25%, is suitable for most applications. In other words, the variance of strut thickness from ring to ring changes (i.e., increases or decreases) in an amount in the range. Generally, it is possible to have a gradient ratio of about 4:1, wherein gradient ratio is defined as the ratio or the largest strut thickness to the smallest strut thickness.

The preferred stent in accordance with the present invention incorporates further features of the stent disclosed in co-pending International Patent Applications PCT/CA97/00151 and PCT/CA97/00152, referred to and incorporated by reference hereinabove.

Thus, in one embodiment, the present stent comprises a plurality of intersecting members comprising a series of longitudinal struts disposed substantially parallel to the longitudinal axis of the stent, each of the longitudinal struts comprising flexure means for substantially complementary extension and compression of a diametrically opposed pair of the longitudinal struts upon flexure of the stent. The use of flexure means in the series of longitudinal struts leads to a very desirable balance of lateral flexibility of the unexpanded stent and radial rigidity of the expanded stent. Practically, the flexure means confers lateral flexibility to the unexpanded stent by allowing diametrically opposed pairs of the longitudinal struts to undergo substantially complementary extension and compression. If one considers a stent in a flexed state, a first longitudinal strut disposed at the tangent of the bend (i.e., in two dimensions) will expand in response to the bending moment. In contrast, a second longitudinal strut disposed diametrically opposite (this can mean above, below or in the same radial plane as) the first longitudinal strut will compress in response to the bending bend moment.

Generally, the degree of extension and compression will be substantially complementary. In other words, in most cases, the first longitudinal strut will expand and lengthen a first distance and the second longitudinal strut will compress and shorten a second distance. Preferably, the first distance is greater than the second distance and most preferably, the sum of the first distance and the second distance is substantially equal to the sum of the original lengths in the first longitudinal strut and the second longitudinal strut.

The specific shape of the flexure means disposed in the longitudinal strut is not particularly restricted provided that it confers lateral flexibility to the unexpanded stent by allowing diametrically opposed pairs of the longitudinal struts to undergo substantially complementary extension and compression. The term "diametrically opposed pairs of the longitudinal struts", as used in this specification, is intended to have a broad meaning. Thus, the "pair" can include opposed struts in the same horizontal plane (i.e., the same ring of polygons) or in different horizontal planes (e.g., one strut in a first ring of polygons and the other diametrically opposed strut in a second ring of polygons above or below the first ring). Preferably, the flexure means comprises at least one lateral section disposed in the longitudinal strut, more preferably at least a first lateral section and a second lateral section disposed in the longitudinal strut. By "lateral section" is meant a section of the longitudinal strut which is bowed in or out (i.e., radially from) the strut. The apex of the lateral section may be pointed, rounded or substantially flat. When the flexure means comprises a first lateral section and a second lateral section, the two sections may be symmetric or asymmetric (in the case of asymmetric this includes two sections of the same shape but different size and two sections of different and size). Further, when the flexure means comprises a first lateral section and a section lateral section, the sections may be bowed in the same or opposite direction.

A particularly preferred embodiment of the flexure means comprises a sinusoidal or S-shaped section (various examples of such a section are illustrated herein and discussed below). Preferably, the sinusoidal or S-shaped section is adjacent the second apex of the polygon and the remaining portion of the strut is substantially straight. This feature improves the lateral flexibility of the stent thereby facilitating implantation thereof and may further mitigate longitudinal shortening of the stent upon expansion.

In another preferred embodiment, at least one, more preferably both, of the side walls (i.e., longitudinal struts) of the polygon comprises the sinusoidal or S-shaped section. Preferably, the sinusoidal or S-shaped section is disposed at an end of the side wall. This feature improves the lateral flexibility of the stent thereby facilitating implantation thereof and may further mitigate longitudinal shortening of the stent upon expansion.

When a sinusoidal or S-shaped portion is disposed in the side walls and/or the strut connecting the first apex and the second apex (if present), the precise shape of the portion is not particularly restricted and generally takes the form of an "S". Thus, the sinusoidal or S-shaped portion may be comprised of a pair of joined curved sections wherein each curved section has an arc of about 1800—i.e., this is illustrated in FIG. 8 of International Patent Applications PCT/CA97/00151 and PCT/CA97/00152. The term "arc" denotes the angle from one end of the curved section to the other about the radical point of the curved section. Alternatively, the sinusoidal or S-shaped portion may be comprised of a pair of joined curved sections wherein each curved section has an arc of greater than 1800—this is illustrated in FIG. 1 of the present application. Further, the pair of joined curved sections can be of the same size or differing size, the latter being the most preferred embodiment.

Preferably, the series of longitudinal struts containing the flexure means comprises all substantially longitudinal struts comprised in the plurality of intersecting members making up the porous surface of the stent.

As discussed above, it is preferred to manifest the gradient of strut thickness in the present stent a plurality of circumferentially disposed rings of a repeating pattern of struts. Preferably, in this embodiment of the present invention, the intersecting members are arranged to define a first repeating pattern comprised of a polygon having a pair of side walls substantially parallel to the longitudinal axis (i.e., a pair of the above-mentioned longitudinal struts comprising flexure means), a concave-shaped first wall having a first apex and a convex-shaped second wall having a second apex connecting the side walls. As used throughout this specification, the terms "concave-shaped" and convex shaped" are intended to have a broad meaning and a shape having apex. Thus, the first wall has a first apex and the second wall has a second apex. Thus, the first apex (i.e., of the concave-shaped first wall) is directed into the polygon whereas the second apex (i.e., of the convex-shaped second wall) is directed away from the polygon.

Preferably, one or both of the first apex and the second apex is flat. The use of such a first repeating pattern (including at least one of the first apex and the second apex being substantially flat), with or without the flexure means present in the side walls of the polygon in the first repeating pattern, results in an improved stent.

The advantages associated with the use of such a first repeating pattern include the following:
1. the force required to expand the stent is substantially reduced;
2. the stent is subjected to less traumatic stress during expansion;
3. plastic deformation of the stent during expansion is facilitated;
4. construction of the stent is facilitated; and
5. upon expansion of the stent, warpage of the first apex and the second apex is obviated or mitigated.

The provision of at least one of the first apex and the second apex being substantially flat usually results in the apex of the concave-shaped first wall and/or the convex-shaped second wall having a pair of shoulders. Preferably, these shoulders are rounded. The provision of such round shoulders results in the following additional advantages:

6. mitigation of potential trauma to the target body passageway from: (i) endoluminal contents within the passageway, and (ii) the contours of the passageway;
7. the resulting expanded stent is more stream-lined and flow directed which mitigates potential trauma to the target body passageway;
8. further reduction in the force required to expand the stent;
9. an improved stent expansion ratio is achieved (i.e., ratio of expanded stent diameter at maximum expansion to unexpanded stent diameter);
10. upon expansion of the stent, the concave-shaped first wall and the convex-shaped second wall are in a substantially orthogonal relationship to the longitudinal axis thereby improving the rigidity of the stent (this is very important to mitigate the occurrence of stent recoil); and
11. the pattern of the expanded stent improves the rheology of fluid flow in the body passageway.

When the stent of the present invention includes the above-mentioned first repeating pattern, it is preferred to provide a connecting strut between the first apex and the second apex. Generally, the connecting strut will be substantially longitudinal (i.e., it will be parallel to the longitudinal axis of the stent). This feature mitigates lifting of the shoulders referred to above as the stent is flexed, for example, when passing the stent through a curved body passageway. The result of this is that potential trauma to the body passageway is mitigated since scraping of the body passageway by the shoulders is mitigated.

In a preferred embodiment, the connecting strut is curved with respect to the longitudinal axis (this is described and illustrated hereinbelow). Preferably, the strut is sufficiently curved to have a length of up to about 35%, more preferably up to about 15%, even more preferably in the range from about 2% to about 8%, most preferably in the range of from about 3% to about 7%, greater than the distance between the first apex and the second apex. This feature improves the lateral flexibility of the stent thereby facilitating implantation thereof. In some cases, the curvature may be designed to comprise the flexure means discussed above. In other words, the shape of the curvature may be designed substantially complementary extension and compression of the connecting strut upon flexure of the stent.

Yet another preferred feature of the stent of the present invention is the provision of one or both of the side walls of the polygon of the repeating pattern being curved. Preferably, both side walls are curved. More preferably the curvature serves as flexure means as described above. Ideally, the curved side wall has length of up to about 35%, more preferably up to about 15%, even more preferably in the range of from about 2% to about 8%, most preferably in the range of from about 3% to about 7%, greater than the distance between the termini of the concave-shaped first wall and the concave-shaped second wall.

This feature improves the lateral flexibility of the strut thereby facilitating implantation thereof.

Preferably, both the strut and the side walls are curved. More preferably, each of the curved members are of substantially the same length.

Yet another preferred feature of the stent of the present invention is, in addition to the strut and side walls of the polygon being curved, the provision of all longitudinal walls of the polygon of the repeating pattern being curved. Thus, in this embodiment of the invention, the concave-shaped first wall comprises a pair of curved first apex walls connecting the first apex and the side walls of the polygon, and the convex-shaped second wall comprises a pair of curved second apex walls connecting the second apex and the side walls of the polygon. Again, in some cases, the curvature may be designed to comprise the flexure means discussed above. Ideally, the curved first apex walls and the curved second apex walls each have a length of up to about 35%, more preferably up to about 15%, even more preferably in the range of from about 2% to about 8%, most preferably in the range of from about 3% to about 7%, greater than the straight (i.e., noncurved) distance between the first apex and the side walls, and the second apex and the side walls, respectively. In this embodiment, it is further preferred to have substantially all adjacent curved walls in an annular section of the repeating pattern (i.e. of the struts, first apex wall, second apex wall and aide walls) are substantially equidistant from one another. This preferred feature of the stent of the present invention even further enhances the lateral flexibility of the stent thereby further facilitating implantation thereof.

The stent of the present invention can further compromise coating material thereon. The coating material can be disposed continuously or discontinuously on the surface of the stent. Further, the coating may be disposed on the interior and/or exterior surface(s) of the stent. The coating material can be one or more of a biologically inert material (e.g., to reduce the thrombogenicity of the stent), a medicinal composition which leaches into the wall of the body passageway after implantation (e.g., to provide anticoagulant action, to deliver a pharmaceutical to the body passageway and the like) and the like.

The stent is preferably provided with a biocompatible containing, in order of minimize adverse interaction with the walls of the body vessel and/or with the liquid, usually blood, flowing through the vessel. The coating is preferably a polymeric material, which is generally provided by applying to the stent a solution or dispersion of preformed polymer in a solvent and removing the solvent. Non-polymeric coating material may alternatively be used. Suitable coating materials, for instance polymers, may be polytetraflouroethylene or silicone rubbers, or polyurethanes which are known to be biocompatible.

Preferably however the polymer has zwitterionic pendant groups, generally ammonium phosphate ester groups, for instance phosphoryl choline groups or analogues thereof. Examples of suitable polymers are described in International Application Number WO-A-93-/16479 and WO-A-93/15775, the contents of each of which are hereby incorporated by way of reference. Polymers described in those specifications are hemo-compatible as well as generally biocompatible and, in addition, are lubricious. It is important to ensure that the surfaces of the stent are completely coated in order to minimize unfavorable interactions, for instance with blood, which might lead to thrombosis.

This good coating can be achieved by suitable selection of coating conditions, such as coating solution viscosity, coating technique and/or solvent removal step.

In another embodiment of the invention, the stent may be joined to a polymer material. Specifically, a polymer material may be extruded onto the stent in such a manner that it envelops at least a portion of the stent. This technique may be used to join two or more stents with a flexible polymeric tube.

This technique may also be used to join a stent to another prosthetic device such as a tube, a graft and the like. Thus, in this embodiment of the invention, the stent is incorporated into an endoluminal prosthesis.

In yet another embodiment of the invention, the stent may be secured (e.g., by suturing) to an existing endoluminal prosthesis such as Gortex™ material or to biological material such as basilic vein. In this regard, securing of the stent to the existing endoluminal prosthesis or biological material may be facilitated by designing the stent such that an end of the stent comprises an annular row of the above-mentioned polygons is having a convex-shaped wall with a flat apex.

With reference to FIG. 1, there is illustrated a preferred embodiment of a two dimensional representation of a repeating pattern usual in the present stent.

The repeating pattern is manifested in a wall 10 disposed between the proximal end and the distal end of the stent (not shown). As illustrated, tubular wall 10 is porous. The porosity of tubular wall 10 is defined by a plurality of intersecting members 15. Intersecting members 15 define a first repeating pattern designated A in FIG. 1.

As illustrated and with further reference to FIG. 1, repeating pattern A is a polygon comprising a pair of side walls 35,40. Side walls 35,40 are substantially parallel to a longitudinal axis of the stent and thus side walls 35,40 may be considered to be longitudinal struts. Side walls 35,40 are connected by a concave-shaped wall 50 and a convex-shaped wall 60. Further, side walls 35,40 include a pair of sinusoidal (or S-shaped) portions 36,41, respectively, adjacent convex-shaped wall 60. This preferred feature enhances the lateral flexibility of the stent. It should be noted that each sinusoidal (or S-shaped) portion 36,41 in FIG. 1 comprises a pair of adjoined curved sections wherein each curved section has an arc of greater than 1800—another way to conceptualize this is a pair of link omega-shaped sections. Further as illustrated, concave-shaped wall 50 and convex-shaped wall 60 are not equidistant along an axis normal to the longitudinal axis of the stent (not shown).

As illustrated, concave-shaped wall 50 is made up of a trio of segments 52,54,56. In the illustrated embodiment, segment 54 is the apex of concave shaped wall 54. As is evident, segment 54 is a flat apex and results in the provision of a pair of substantially rounded shoulders 57,58. Convex-shaped wall 60 is made up of a trio of segments 62,64,66. In the illustrated embodiment, segment 64 is the apex of convex-shaped wall 60.

It will be appreciated by those of skill in the art that the provision of first repeating pattern A, as illustrated, necessarily defines and provides for a second repeating pattern B. It will also be appreciated by those of skill in the art that second repeating pattern B is a mirror image of first repeating pattern A taken along an axis (not shown) substantially normal to longitudinal axis of the stent.

Thus, in the illustrated embodiments, adjacent rows of repeating pattern A and repeating pattern B may be considered to be interlocking polygons of "arrowheads".

To facilitate an understanding of the present stent, repeating pattern A in FIG. 1 has been designated as circumferential rings I,II,III,IV,V (for clarity, repeating pattern A has not been labeled in circumferential rings I and II).

Further, in circumferential rings I,II of repeating pattern A, a strut 70 has been added to connect segment 54 of concave-shaped wall 50 and segment 64 of convex-shaped wall 60—this may be regarded as a "closed design". Further, strut 70 includes sinusoidal (or S-shaped) portion 71 adjacent flat apex of concave shaped wall 50. Thus, strut 70 may be considered as a relatively thin retention segment which reconciles the need for retaining flexibility in the strut with mitigating lifting of rounded shoulders 57,58 when the stent is delivered to the target body passageway through a relatively tortuous route. As will be apparent, circumferential rings III,IV,V of repeating pattern A do not include strut 70—this may be regarded as an "open design". Thus, the terms "closed design" and "open design" design are used in a relative sense.

It should be noted that each sinusoidal (or S-shaped) portion 36,41,71 in FIG. 1 comprises a pair of adjoined curved sections wherein each curved section has an arc of greater than 1800. Further, the curved sections in sinusoidal (or S-shaped) portion 71 are of different size. A distinct advantage of the interspersion of sinusoidal (or S-shaped) portions 36,41 and sinusoidal (or S shaped) portion 71 in circumferential rings I,II is that substantially uniform radial expansion of all segments in this stent will occur without specific regard to the expansion forces generated by the balloon or other means used to deploy the stent. Further, this design minimizes the force (e.g., pressure from a balloon) required to expand the stent. Still further, this design enhances the lateral flexibility of the stent.

As will be apparent to those of skill in the art, sinusoidal (or S-shaped) portion 71 is offset with respect to sinusoidal (or S-shaped) portions 36,41 in a plane horizontal to the longitudinal axis of tubular wall 10. The offset nature of these sinusoidal (or S-shaped) portions serves to increase the bending points in the stent allowing the stent to bend while avoiding buckling thereof. Thus, the staged distribution of the sinusoidal (or S-shaped) portions over a large portion of the surface area of the stent serves to improve the flexibility of the stent.

In the illustrated embodiment, the gradient of strut thickness is manifested in concave-shaped wall 50 and convex-shaped wall 60 only in circumferential rings I,II,III,IV,V. In other words side walls 35,40 and strut 70 (if present) are of substantially the same thickness from circumferential ring to circumferential ring.

Thus, the thickness of concave-shaped wall 50 and convex-shaped wall 60 decreases from circumferential ring I to circumferential ring V. This results in an increase of the radial rigidity of the expanded stent toward circumferential ring I. As shown thickness decreases about 20% from circumferential ring to circumferential ring. The gradient of strut thickness is not manifested in side walls 35,40 and strut 70 in the illustrated embodiment since this would effect the flexibility of the stent and the advantages accruing from the provision of sinusoidal (or S-shaped) portions 36,41 and sinusoidal (or S-shaped) portion 71.

However, it will be clearly understood that there may be stent designs in which it is appropriate and advantageous to manifest the gradient of strut thickness in a struts comprised in the circumferential ring.

It will be further appreciated by those of skill in the art that the shape of concave-shaped wall 50 and/or convex-shaped wall 60 can be modified without departing from the function and performance of the stent provided that at least one of concave-shaped wall 50 and convex-shaped wall 60 retain a substantially flat apex. For example, the trio of segments can be replaced by a suitably curved or arcuate wall. Alternatively, more than three segments can be used to define concave-shaped wall 50 and/or convex-shaped wall 60. Other modifications will be apparent to those of skill in the art.

It will be further appreciated by those of skill in the art that various walls of first repeating pattern A and second repeating pattern B may be omitted (and even desired) at selected points along the body of the stent without departing from the spirit and scope of the invention. For example, it is possible to omit one or both of side walls 35 and 40 at selected points along the body of the stent with a view to improving the longitudinal flexibility of the stent. Further, it is possible to omit one or more of segments 62,64,66 at selected points along the body of the stent with a view to improving the lateral flexibility of the stent.

Still further, the design depicted in FIG. 1 can be modified to omit, on a selected basis, first repeating pattern A and/or second repeating B with a view to improve flexibility of the stent and to allow access to other structures (e.g., side branches/arteries) outside the bounds of the stent.

As discussed above, the use of flexure means, such as the sinusoidal (or S-shaped) portions in the longitudinal struts in the stent design provides the added benefit of improved flexibility of the stent in the unexpanded state. Specifically, during flexure of the stent, provision of such a feature allows the inner stent surface adjacent the bend to compress while concurrently allowing the outer stent surface adjacent the bend to extend, all while maintain substantially intact the integral strength of stent and avoiding buckling of the stent.

The amplitude gradient embodiment of the invention can be produced by modifying the design illustrated in FIG. 1 in the following manner:
  (i) struts 15 throughout wall 10 have substantially the same thickness; and (ii) the amplitude of repeating pattern A is reduced incrementally from circumferential ring I to circumferential ring V (i.e., side walls 35,40 are shortened resulting in a reduction in the longitudinal distance between segments 54 and 64 from circumferential ring or circumferential ring).

This results in an increase in the radial rigidity of the stent toward circumferential ring V. This is believed to occur due to an increase in the frequency of the repeating pattern over a given longitudinal distance as the amplitude thereof is decreased.

It is believed that a gradient of repeating pattern amplitude (i.e., the increase or decrease of the amplitude of the repeating pattern) from ring to ring in the range of from about 5% to about 50%, preferably from about 10% to about 40%, more preferably from about 15% to about 25%, is suitable for most applications. In other words, the variance of repeating pattern amplitude from ring to ring changes (i.e., increases or decreases) in an amount in the range.

Generally, it is possible to have a gradient ratio of about 4:1, wherein gradient ratio is defined as the ratio of the largest amplitude of the repeating pattern to the smallest amplitude of the repeating pattern.

The manner by which the present stent is manufactured is not particularly restricted. Preferably, the stent is produced by laser cutting techniques applied to a tubular starting material. Thus, the starting material could be a thin tube of a metal or alloy (non-limiting examples include stainless steel, titanium, tantalum, nitinol, Elgiloy, NP35N and mixtures thereof which would then have sections thereof cut out to leave repeating pattern A discussed above. Thus, the preferred design of the present stent is one of a tubular wall which is distinct from prior art wire mesh designs where wire is conformed to the desired shape and welded in place. The preferred tubular wall design of the present stent facilitates production and improves quality control by avoiding the use of welds and, instead, utilizing specific cutting techniques.

Preferably, the stent is coated with a solution of 1:2 (mole) copolymer of (methacryloyloxy ethyl)-2-(trimethylammonium ethyl) phosphate inner salt with lauryl methacrylate in ethanol (as described in Example 2 of International patent application WO-A-93/01221 as follows. The non-expanded stent may be placed in a tube having a slightly larger diameter than the stent. The tube may then be filled with coating solution and the solution allowed to drain steadily from the tube to form a completely coated stent. Immediately thereafter a stream of warm air or nitrogen may be directed through the tube at a linear velocity of 0.1.5 m/s at room temperature to 500° C. for a period of 30 seconds to 5 minutes to dry the coating by evaporation of the ethanol solvent.

As an alternative or in addition (on top or underneath) to this coating, a cross-linkable coating may be used consisting of a polymer of 23 mole % (methacryloyloxy ethyl)-2-(trimethylammonium ethyl) phosphate inner salt, 47 mole % lauryl methacrylate, 5 mole % trimethoxysilylpropyl methacrylate and 25 mole % of hydroxypropyl methacrylate. This may be applied to the stent by the above described technique from a 5 mg/ml ethanoic solution. The solution may be dried as described above and then cured by heating at 70 to 75° C. for a period of at least about an hour, for instance overnight. This curing generally results in substantially complete reaction of the methoxy silyl groups, either with other methoxy silyl groups or with hydroxy groups derived from the hydroxypropyl methacrylate monomer, driving off methanol. In one preferred embodiment the crosslinkable coating is applied to the cleared stent, cured and then a further coating of the lauryl methacrylate copolymer described above is applied.

The coated stent may be sterilized by ethylene oxide, gamma radiation or electron beam and subsequently mounted onto a balloon catheter for delivery.

The present stent can be implanted using a conventional system wherein a guidewire, catheter and balloon can be used to position and expand the stent.

Implantation of mono-tubular stents such as stent is conventional and within the purview of a person skilled in the art. See, for example, any one of the U.S. Pat. Nos. 4,733,665, 4,739,762, 5,035,706, 5,037,392, 5,102,417, 5,147,385, 5,282,824, 5,316,023 and any of the references cited therein or any of the references cited hereinabove.

It will be apparent to those of skill in the art that implantation of the present stent can be accomplished by various other means. For example, it is contemplated that the stent can be made of suitable material which will expand when a certain temperature is reached. In this embodiment, the material may be a metal alloy (e.g., nitinol) capable of self-expansion at a temperature of at least about 30° C., preferably in the range of from about 30° C. to about 40° C. In this embodiment, the stent could be implanted using a conventional catheter and the radially outward force exerted on the stent would be generated within the stent itself. Further, the present stent can be designed to expand upon the application of mechanical forces other than those applied by a balloon/catheter. For example, it is possible to implant the present stent using a catheter equipped with a resisting sleeve or retaining membrane which may then be removed with the catheter once the stent is in position thereby allowing the stent to expand. Thus, in this example, the stent would be resiliently compressed and would self-expand once the compressive force (i.e., provided by the sleeve or membrane) is removed.

A particular advantage during implant of the present stent is that, during expansion, the end thereof which is opposite the more radially rigid end of the stent is initially urged against the body lumen preliminarily securing the stent in position which assists in the placement and expansion of the more radially rigid end of the stent.

While this invention has been described with reference to illustrative embodiments, this description is not intended to be construed in a limiting sense.

Various modifications of the illustrative embodiments, as well as other embodiments of the invention, will be apparent to persons skilled in the art upon reference to this description. For example, while the illustrated embodiment incorporates both a "closed design" and an "open design", it is possible to produce the stent having only a "closed design" or an "open design". Further, while specific embodiment has been shown for illustrative purposes only, those of skill in the art will immediately recognize that the advantages of the gradient of strut thickness transcend specific stent design and can be incorporated in many known stent designs vastly improving such stent designs. Further, the strut gradient embodiment and the amplitude gradient embodiment can be combined in a single stent design. It is therefore contemplated that the appended claims will cover any such modifications or embodiments.

What is claimed is:

1. An expandable stent comprising:
   a proximal end and a distal end in communication with one another,
   a tubular wall disposed between the proximal end and the distal end, the tubular wall having a longitudinal axis and a porous surface defined by a plurality of interconnected struts,
   the plurality of interconnected struts defining a plurality of circumferentially disposed rings of a repeating pattern,
   adjacent circumferentially disposed rings of the repeating pattern comprising a gradient of strut thickness when measured along the outer surface of the tubular wall,
   the plurality of interconnected struts also defining a plurality of longitudinal struts disposed substantially parallel to the longitudinal axis of the stent, each of the longitudinal struts comprising curved flexure structure for substantially complementary extension and compression of a diametrically opposed pair of the longitudinal struts upon flexure of the stent, the curved flexure structure disposed between the adjacent circumferentially disposed rings having substantially no gradient of strut thickness, each curved flexure structure comprising at least one curved portion disposed between two straight portions, both of which are substantially co-linear and substantially parallel to the longitudinal axis,
   the stent being expandable from a first, contracted position to a second, expanded position upon the application of a radially outward force on the stent.

2. The stent defined in claim 1, wherein the flexure structure includes at least one lateral section disposed in each longitudinal strut.

3. The stent defined in claim 2, wherein the at least one lateral section comprises a rounded apex.

4. The stent defined in claim 1, wherein the flexure structure includes at least a first lateral section and at least a second lateral section disposed in each longitudinal strut.

5. The stent defined in claim 1, wherein the gradient of strut thickness comprises a change in thickness of struts between adjacent circumferentially disposed rings of the repeating pattern.

6. The stent defined in claim 5, wherein the gradient of strut thickness is manifested between all struts in adjacent circumferentially disposed rings of the repeating pattern.

7. The stent defined in claim 1, wherein the repeating pattern comprises a first repeating pattern.

8. The stent defined in claim 1, wherein the repeating pattern comprises a first repeating pattern and a second repeating pattern different from the first repeating pattern.

9. The stent defined in claim 1, wherein the repeating pattern comprises a polygon having a pair of side walls substantially parallel to the longitudinal axis.

10. The stent defined in claim 9, wherein the flexure structure is disposed in each of the side walls.

11. The stent defined in claim 9, wherein the polygon further comprises a concave-shaped wall and a convex-shaped wall connected to each other by the pair of side walls.

12. The stent defined in claim 11, wherein the gradient of strut thickness is manifested in the concave-shaped wall.

13. The stent defined in claim 11, wherein the gradient of strut thickness is manifested in the convex-shaped wall.

14. The stent defined in claim 11, wherein the concave-shaped first wall has a first apex and the convex-shaped second wall has a second apex.

15. The stent defined in claim 11, wherein both the first apex and the second apex are substantially flat.

16. The stent defined in claim 15, wherein the first apex and the second apex are of different length.

17. The stent defined in claim 15, wherein the first apex and the second apex are of the same length.

18. The stent defined in claim 11, wherein one of the side walls is curved with respect to the longitudinal axis.

19. The stent defined in claim 18, wherein the one of the side walls which is curved has a length up to about 35% greater than the distance between the respective termini of the first wall and the second wall.

20. The stent defined in claim 18, wherein the one of the side walls which is curved has a length up to about 15% greater than the distance between the respective termini of the first wall and the second wall.

21. The stent defined in claim 18, wherein the one of the side walls which is curved has a length in the range of from about 2% to about 8% greater than the distance between the respective termini of the first wall and the second wall.

22. The stent defined in claim 18, wherein the one of the side walls which is curved has a length in the range of from about 3% to about 7% greater than the distance between the respective termini of the first wall and the second wall.

23. The stent defined in claim 11, wherein both of the side walls are curved with respect to the longitudinal axis.

24. The stent defined in claim 23, wherein the side walls have a length up to about 35% greater than the distance between the respective termini of the first wall and the second wall.

25. The stent defined in claim 23, wherein the side walls have a length up to about 15% greater than the distance between the respective termini of the first wall and the second wall.

26. The stent defined in claim 23, wherein the side walls have a length in the range of from about 2% to about 8% greater than the distance between the respective termini of the first wall and the second wall.

27. The stent defined in claim 23, wherein the side walls have a length in the range of from about 3% to about 7% greater than the distance between the respective termini of the first wall and the second wall.

28. An expandable stent comprising:
   a tubular wall having a plurality of circumferentially disposed struts interconnected by a plurality of longitudinally disposed struts;
   at least two adjacent circumferentially disposed struts having different strut thicknesses, when measured along the outer surface of the tubular wall;
   the plurality of longitudinally disposed struts which extend between said at least two adjacent circumferentially disposed struts having substantially the same strut thicknesses, when measured along the outer surface of the tubular wall; and
   each of said plurality of longitudinally disposed struts which extend between said at least two adjacent circumferentially disposed struts comprising at least one curved portion disposed between two straight portions, both of which are substantially co-linear and substantially parallel to the longitudinal axis.

* * * * *